United States Patent
Krieger

(10) Patent No.: US 9,375,738 B2
(45) Date of Patent: Jun. 28, 2016

(54) DISPENSER FOR DISCHARGING AN IN PARTICULAR GRANULAR OR POWDERY SUBSTANCE, USE OF A SUCKING/BLOWING DISPENSER, AND METHOD FOR EMPTYING A SUBSTANCE RESERVOIR

(71) Applicant: RPC Formatec GmbH, Mellrichstadt (DE)

(72) Inventor: Johannes Krieger, Mellrichstadt (DE)

(73) Assignee: RPC Formatec GmbH, Mellrichstadt (DE)

( * ) Notice: Subject to any disclaimer, the term of this patent is extended or adjusted under 35 U.S.C. 154(b) by 0 days.

(21) Appl. No.: 14/390,440

(22) PCT Filed: Apr. 5, 2013

(86) PCT No.: PCT/EP2013/057166
§ 371 (c)(1),
(2) Date: Oct. 3, 2014

(87) PCT Pub. No.: WO2013/150129
PCT Pub. Date: Oct. 10, 2013

(65) Prior Publication Data
US 2015/0041489 A1 Feb. 12, 2015

(30) Foreign Application Priority Data
Apr. 5, 2012 (DE) .......................... 10 2012 103 000

(51) Int. Cl.
*B05B 11/06* (2006.01)
*A61M 11/06* (2006.01)
(Continued)

(52) U.S. Cl.
CPC ............ *B05B 11/061* (2013.01); *A61M 11/007* (2014.02); *A61M 11/06* (2013.01);
(Continued)

(58) Field of Classification Search
CPC .. B05B 11/061; B05B 11/064; B05B 11/067; B05B 7/0012; B05B 7/1486; B05B 7/1472; A61M 11/007; A61M 11/02; A61M 11/06; A61M 15/0036; A61M 15/0015; A61M 15/002; A61M 15/0045; A61M 2205/073
USPC ................................... 222/631, 82, 144, 168
See application file for complete search history.

(56) References Cited

U.S. PATENT DOCUMENTS

| 1,406,903 A * | 2/1922 | Rose ..................... B05B 11/062 222/195 |
| 2,950,564 A * | 8/1960 | Bonine ................. B05B 11/062 222/195 |

(Continued)

FOREIGN PATENT DOCUMENTS

| CA | 2 681 335 A1 | 3/1997 |
| DE | 31 20 250 A1 | 6/1982 |

(Continued)

OTHER PUBLICATIONS

International Search Report of PCT/EP2013/057166, mailed Jul. 8, 2013.

*Primary Examiner* — Nicholas J Weiss
(74) *Attorney, Agent, or Firm* — Collard & Roe, P.C.

(57) ABSTRACT

A dispenser for discharging an in particular granular or powdery substance by blow-out, has a blow-out duct, and a suction line opening into the blow-out duct for sucking the substance into the blow-out duct. A positive air pressure can be built up in a duct section arranged upstream of the blow-out duct and closed in the direction of the blow-out duct by a valve opening in a pressure-dependent manner, for pressure-controlled formation of a blow-out stream in the blow-out duct. A method for emptying a substance reservoir having a freeze-dried substance sucks the substance out of the substance reservoir, using a suction air stream opening into a blowing stream, and discharges the substance. A sucking/blowing dispenser is used for emptying a substance reservoir having a freeze-dried substance.

7 Claims, 1 Drawing Sheet

(51) Int. Cl.
*B05B 7/00* (2006.01)
*B05B 7/14* (2006.01)
*A61M 15/00* (2006.01)
*A61M 11/00* (2006.01)

(52) U.S. Cl.
CPC ........ *A61M 15/002* (2014.02); *A61M 15/0015* (2014.02); *A61M 15/0045* (2013.01); *B05B 7/0012* (2013.01); *B05B 7/1486* (2013.01); *B05B 11/064* (2013.01); *B05B 11/067* (2013.01); *A61M 2205/073* (2013.01)

(56) References Cited

U.S. PATENT DOCUMENTS

| | | | |
|---|---|---|---|
| 3,856,185 A | 12/1974 | Riccio | |
| 4,386,445 A | 6/1983 | Rudolf | |
| 5,447,151 A * | 9/1995 | Bruna | A61M 15/0045 128/203.15 |
| 5,568,884 A * | 10/1996 | Bruna | A61M 15/0065 128/203.13 |
| 5,645,050 A * | 7/1997 | Zierenberg | A61M 15/0045 128/200.22 |
| 6,003,512 A * | 12/1999 | Gerde | A61M 15/00 128/203.15 |
| 6,691,892 B2 * | 2/2004 | Odessa | B05B 11/062 222/1 |
| 2010/0252656 A1 | 10/2010 | Gerbron et al. | |

FOREIGN PATENT DOCUMENTS

| | | |
|---|---|---|
| DE | 195 00 764 A1 | 7/1996 |
| DE | 196 13 130 A1 | 3/1997 |
| DE | 196 12 561 A1 | 9/1997 |
| FR | 2 082 780 A5 | 12/1971 |
| FR | 2 918 299 A1 | 1/2009 |
| GB | 1 274 154 A | 5/1972 |
| WO | 90/07351 A1 | 7/1990 |

* cited by examiner

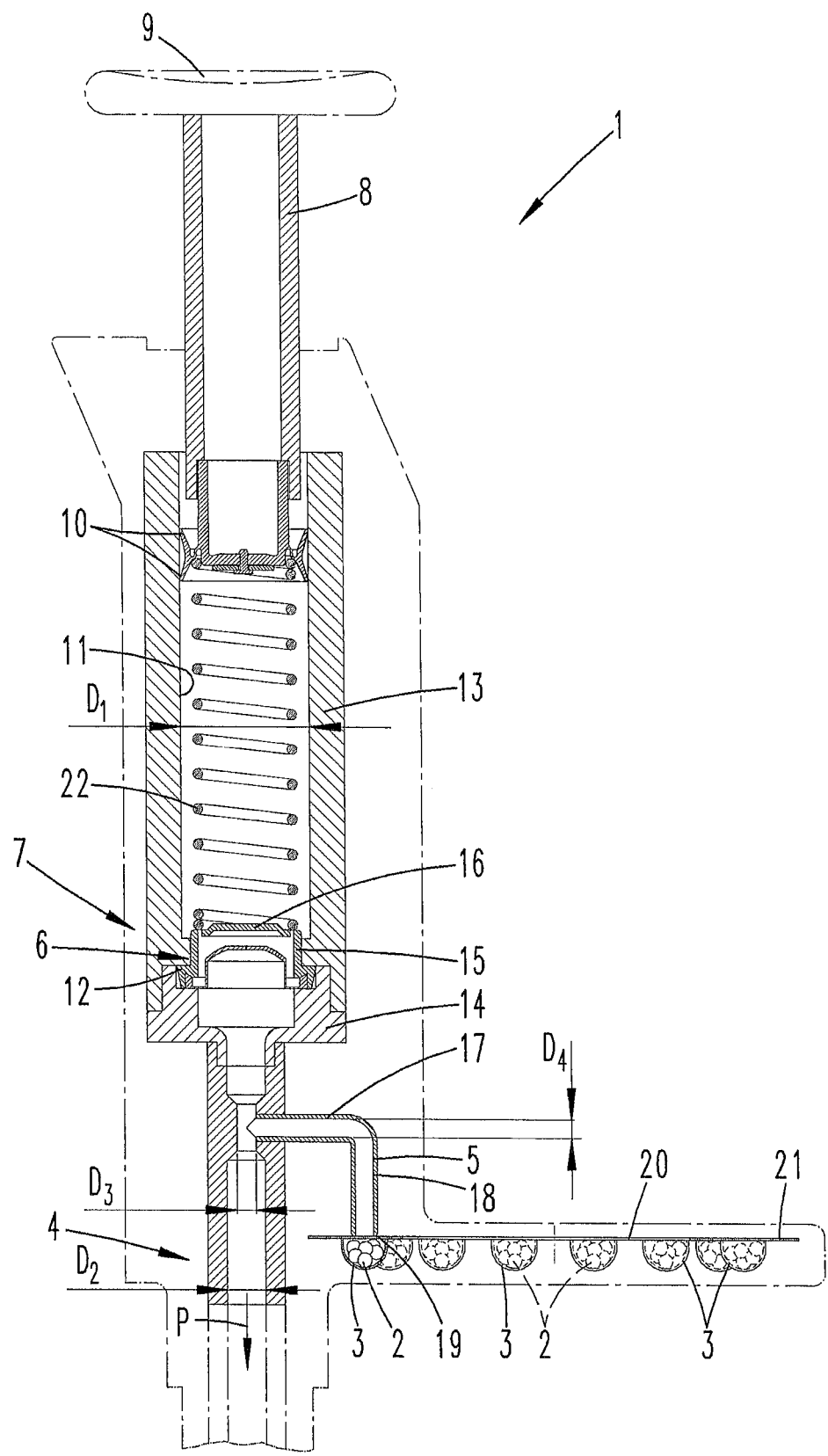

and with a suction line opening into the blow-out duct for sucking the substance into the blow-out duct, wherein a positive air pressure can be built up in a duct section arranged upstream of the blow-out duct and closed in the direction of the blow-out duct by a valve opening in a pressure-dependent manner, for pressure-controlled formation of a blow-out stream in a blow-out duct, wherein moreover the dispenser has a seat for a substance storage part, and a substance storage part, wherein the substance storage part has a plurality of substance reservoirs, and the suction line has a mouth.

The invention further relates to a use of a sucking/ blowing dispenser according to one of the material claims and a method for emptying a dispenser according to one of the material claims.

FR 2 082 780 A discloses a two-stage grinder for lyophilization parts. Larger lyophilization parts, initially contained in a storage space, are forced by means of a piston against a rotating grinder disk. The smaller particles thereby generated are sucked through a line into a second grinder in accordance with the Venturi principle. The Venturi principle is realized by a pressure line interrupted for suitable inward suction. DE 195 00 764 A1 is additionally cited as prior art.

In relation to the stated prior art, the object of the invention is to make available an advantageous dispenser for discharging an in particular granular or powdery substance by blowout.

It is essential for this purpose, that an air compression piston is movable in the duct section between a rest or start position and an actuation position, in which it is driven close to the valve, and that the suction line has a mouth, which is structured in such a way that it can easily serve to pierce a substance reservoir, wherein moreover the substance reservoir consists of a lower container in the shape of a portion of a sphere, which container is closed at the top by a film in a plane surface.

By compressing the air in the duct section, a certain build-up of pressure can first of all be obtained without a suction stream already being created in the suction channel, and, when the valve opens, this pressure immediately generates a high flow rate in the blow-out duct, which brings with it the desired suction effect in the suction duct and reliably sucks up the desired amount of substance to be discharged and allows this to be dispensed through the blow-out duct. By virtue of the fact that pumping as it were can initially take place until the desired air flow is safely obtainable, such a design is in particular suitable as a manual appliance. An air compression piston, for example, can be moved by finger pressure until the desired positive pressure is reached and the valve opens and the described effect then sets in.

As regards the method, the invention proposes that, with the aid of a dispenser as described above or in a further embodiment described here, the substance from the substance reservoir, the substance being present in the form of grains with a diameter of 0.1 mm to 2 mm, is sucked out by means of a suction air stream opening into the blowing stream generated by pressing with a finger and moving the air compression piston, and is dispensed, wherein the blowing stream is generated by moving the air compression piston until a desired positive pressure arises and the valve opens.

As regards the use, the invention proposes that said sucking/blowing dispenser with the air compression piston movable by finger pressure for generating a desired positive pressure, in which the valve opens and in which, when the valve opens, a high flow rate is immediately generated in the blow-out duct, which brings with it a desired suction effect in the suction line, is used for emptying, via the suction line, the substance reservoir having a freeze-dried substance, wherein the substance is present in the form of grains with a diameter of 0.1 mm to 2 mm.

In particular, it concerns substances which are used in the medical or biological field and which are received in small substance reservoirs, for example blister-sealed cavities. The substance reservoir can also be made relatively small, i.e. for example relative to a sphere, wherein the actual geometry does not need to be spherical, and can have a volume which, in relation to the stated sphere, corresponds to a sphere diameter of 1 mm to 10 mm, for example.

Specifically with respect to such comparatively small amounts and small sizes of the substance reservoir, it has been recognized that such a dispenser, in which the required sucking and blowing stream can moreover be generated by manual operation, can be used particularly favorably.

As regards the valve, it is preferable, for example, that it is a plastic valve. It can in particular be a self-closing valve, as is known from DE 196 13 130 A1 or from DE 196 12 561 A1, for example. The disclosure in these documents is herewith incorporated in full into the disclosure in the present application, in order also to incorporate features of said documents into claims of the present application.

Referring to the illustration in FIG. 4 of DE 196 12 561 A1, which discloses the refilling by suction, it is clear that the valve is as it were "broken open" in a downward direction. Air is sucked in through the upper opening indicated there by reference sign 4, and the air then flows into the container through the opened valve. This valve, which in the rest state adopts a geometry as per FIG. 2 for example, does not open in the sense of FIG. 4 immediately upon a first suction underpressure in the container, but only when a certain level of underpressure is built up, after which it then "breaks open". This property is utilized favorably in the context here, since the suitable configuration of the geometry, for example the thicknesses of the valve walls, makes it possible to expediently determine at which positive pressure the valve breaks open.

In particular, it is preferable that the valve has a lower retaining edge and an upper and substantially concavely extending closure cap, wherein moreover the closure cap and the retaining edge are connected by a connecting wall. The connecting wall can extend conically or also cylindrically. In relation to the injection state, the installation state can be non-inverted with respect to the closure membrane and the connecting wall. This can lead to a particular tensioning in the closure cap. Here, the closure cap can also have a greater thickness at the edge than the connecting wall. Starting from its edge area, the closure cap can taper continuously inward. The connecting wall is bound with respect to a boundary edge appearing in the cross section of the closure cap in the upper area, once again in relation to the installation state, and a lower free boundary area of the boundary edge of the closure cap is at any rate preferably covered by the boundary wall in the installation state.

In further detail, such a valve can, with respect to conventional dispensers known, for example honey dispensers, be installed in such a way that the breaking open of the valve and the creation of the air flow in the blow-out duct correspond to the conventional dispensing procedure. However, provision can also be made that the valve is installed the other way, i.e. that the breaking open as it were in relation to a honey dispenser, for example, corresponds to the resuctioning of air.

As an alternative to this, the valve can also be a conventional spring-loaded ball valve. The spring brings about a pretensioning, which in the same way only permits opening depending on a defined positive pressure.

The dispenser has a seat for a substance storage part, which substance storage part in turn has a plurality of substance reservoirs. This can be a blister part, for example a circular, in particular a ring-shaped blister part which has in a circle shape a plurality of blister cavities in succession. In particular, the substance storage part is also formed in the shape of a circular disk.

As regards the method, the air pressure needed to empty a substance reservoir is built up by manual actuation, for example by means of a pump piston actuated by hand, namely in the sense that the built-up air pressure in the blow-out duct having a comparatively small diameter brings about the required air flow in order to ensure that the substance from the substance reservoir is conveyed out through the suction duct opening into the blow-out duct and is safely conveyed into the blow-out duct.

The ranges or value ranges which are cited above and below include, with respect to the disclosure, also all intermediate values, in particular in 1/10 steps of the respective dimension, where appropriate, therefore, even dimensionless, for example, for a diameter ratio indicated as 0.8 to 0.3, also 0.79 to 0.3 or 0.8 to 0.31 or 0.79 to 0.31, etc., on the one hand for the downward and/or upward confinement of said range limits, alternatively or additionally, however, also with regard to the disclosure of one or more singular values from the respective range indicated.

The invention is explained below with reference to the attached drawing which, however, shows only an illustrative embodiment. In the drawing the single FIGURE shows a cross section through the dispenser and associated substance reservoir.

A dispenser 1 is shown and described for discharging a for example granular substance 2 which is arranged in a substance reservoir 3. The dispenser 1 has a blow-out duct 4 and a suction line 5 that opens into the blow-out duct 4. A valve 6 is arranged upstream of the blow-out duct 4 in the blow-out direction in a duct section 7, which is initially closed in the starting state shown. The dispenser 1 moreover has an air compression piston 8 which is movable in the duct section 7 between a rest or start position, as shown, and an actuation position, in which it is driven close to the valve 6. With the driving of the air compression piston 8 to the valve 6, a positive air pressure builds up between the air compression piston 8 and the valve 6, until the valve 6 opens. With opening of the valve 6, a relatively strong air stream flows through the blow-out duct 4, such that, where the suction line opens into the blow-out duct 4, a suction effect is obtained and air is sucked through the suction line 5 into the blow-out duct 4. Since the suction line 5 protrudes into the substance reservoir 3 in such a dispensing state, substance 2 is thus sucked out of the substance reservoir 3 and, after passing the area where the suction line 5 opens into the blow-out duct 4, is discharged in the blow-out duct 4 in the direction of the arrow P.

At one end, the air compression piston 8 can have an actuation surface 9 for manual actuation of the dispenser 1. In particular, in its start position as shown, the dispenser 1 can have a height or extent in the direction of movement of the air compression piston 8 that corresponds, for example, to twice the width of a hand or is smaller, i.e. at any rate adapted in size to actuation by hand.

Moreover, at the front end, the air compression piston 8 has one or two sealing lips 10 which are in contact with an inner surface 11 of the duct section 7 and thus permit the build-up of the positive air pressure when the air compression piston 8 is moved, specifically downward in the view shown.

The valve 6 is preferably a plastic valve. It preferably has a clamping flange 12 with which it is held sealingly in the housing of the dispenser 1. In the illustrative embodiment, the dispenser 1 for this purpose has an upper part 13 and a lower part 14, which both form a part of the duct section 7. Starting from the clamping flange 12, the valve moreover has a connecting wall in the form preferably of a cylinder portion 15, wherein the valve in the illustrative embodiment is arranged such that the cylinder portion, starting from the clamping flange 12, extends in the direction of the air compression piston 8. The cylinder portion 15 then merges into a closure cap 16 which preferably, as in the illustrative embodiment, extends curving in an arch shape. Here, the closure cap 16 is curved convexly in the direction toward the air compression piston 8. The closure cap 16 moreover has one or more slits, but the slit walls bear against each other in the rest state as shown in the FIGURE.

In the course of the pressure increase as the air compression piston 8 moves in the direction of the valve 6, said arched structure has the effect firstly that the slit walls are pressed closer together, such that the sealing effect of the valve in the first instance tends even to increase.

This takes place until the arch structure no longer withstands the increased pressure and turns downward in the direction of the arrow P, it also being possible for part of the cylinder portion 15 to turn down too. This then leads to an opening or gaping of the slit walls, and the air flows at increased pressure, and therefore also with corresponding flow velocity, into the blow-out duct 4.

In further detail, the duct section 7 has a first diameter $D_1$, while the blow-out duct has a second diameter $D_2$. The second diameter $D_2$ is smaller than the first diameter $D_1$. There is preferably a ratio of 0.8 to 0.3 with respect to $D_2:D^1$.

It is also important that, in the area of entry of the suction line 5, the blow-out duct 4 has, in relation to the diameter $D_2$, a further narrowing with a diameter $D_3$. The diameter $D_3$ is preferably narrowed in the same ratio range as $D_2$ to $D_1$, i.e. $D_3:D_2$ also corresponds to about 0.8 to 0.3.

As regards diameter, it has been assumed that the latter is in each case a free circular cross section in the stated portions. However, cross sections deviating from this could also be provided. In particular, "diameter" then relates to a maximum internal dimension.

The suction line 5 has a diameter $D_4$. $D_4$ can correspond in the first instance to $D_3$. However, it can also be greater than $D_3$ or smaller than $D_3$. It is preferable that $D_4$ is smaller than $D_2$ but greater than $D_3$.

In the cross section, the suction line 5 is clearly formed at an angle, with a first horizontal portion 17 and a second vertical portion 18.

The angle between the portions 17 and 18 does not have to be a right angle. In the illustrative embodiment, however, a right angle is shown.

The suction line 5, or in the illustrative embodiment specifically the vertical portion 18, has at its end a mouth 19, which is preferably also structured in such a way that it can easily serve to pierce a substance reservoir 3. For example, it can have a conical tip having openings. As can be seen, the substance reservoir 3 preferably consists of a lower container in the shape of a portion of a sphere, which container is closed at the top by a film in a plane surface 20. This constitutes a customary blister pack.

With said mouth 19, the suction line 5 can now penetrate a blister cavity by piercing the film, and the substance 2 therefore then lies in the suction stream when the dispenser 1 is activated.

As can also be seen, the substance reservoirs 3 are preferably arranged in a support part 21 which is shaped as a circular ring and which on the top has said film cover and on the bottom has the substance reservoirs 3. Five to fifty or more substance reservoirs 3, for example, can obviously be arranged next to each other in such a support part and can be distributed uniformly about the circular ring.

After substance has been sucked out of a substance reservoir 3, the support part is moved onward in the direction of the circumference of the circle, such that the next adjacent substance reservoir 3 or, if preferable for some reason, a farther away substance reservoir 3 is then available for the next suction procedure. In this case, the support part can first of all be lowered, then rotated in a circular direction and, when a further substance reservoir 3 is oriented with respect to a tip of the suction line, can be raised again, with the tip of the suction line penetrating at the same time into the substance reservoir 3.

The support 21 can be received in a housing part in such a way that it is basically not visible during use of the device. However, the latter can be provided with a window through which, for monitoring purposes, it is possible to see, for example, the substance reservoir 3 from which substance has been previously sucked out after a corresponding advance movement.

In its starting position as shown in FIG. 1, the air compression piston 8 can clearly still be pretensioned by a compression spring 22.

List of Reference Signs
1 dispenser
2 substance
3 substance reservoir
4 blow-out duct
5 suction line
6 valve
7 duct section
8 air compression piston
9 actuation surface
10 sealing lip
11 inner surface
12 clamping flange
13' upper part
14 lower part
15 cylinder portion
16 membrane portion
17 horizontal portion
18 vertical portion
19 mouth
20 surface
21 support
22 compression spring
P arrow
$D_1$ first diameter
$D_2$ second diameter
$D_3$ third diameter
$D_4$ fourth diameter

The invention claimed is:

1. A dispenser (1) for discharging an in particular granular or powdery substance (2) by blow-out, comprising
a blow-out duct (4), and with a suction line (5) opening into the blow-out duct (4) for sucking the substance (2) into the blow-out duct (4),
wherein a positive air pressure can be built up in a duct section (7) arranged upstream of the blow-out duct (4) and closed in the direction of the blow-out duct (4) by a valve (6) opening in a pressure-dependent manner, for pressure-controlled formation of a blow-out stream in the blow-out duct (4),
wherein moreover an air compression piston (8) is movable in the duct section (7) between a rest or start position and an actuation position, in which it is moved close to the valve (6),
wherein there is a substance storage part and the dispenser (1) has a seat for the substance storage part, wherein the substance storage part has a plurality of substance reservoirs (3), and wherein the suction line (5) has a mouth (19), which is structured in such a way that it can easily serve to pierce a substance reservoir (3),
wherein moreover the substance reservoir (3) comprises a lower container in the shape of a portion of a sphere, which container is closed at the top by a film in a plane surface (20).

2. The dispenser as claimed in claim 1,
wherein the substance reservoir (3) is formed in a circular support part (21), and wherein the support part (21) is movable in the circumferential direction of the circle, such that a next adjacent substance reservoir (3), or a farther away substance reservoir (3), is available for a subsequent suctioning.

3. The dispenser as claimed in claim 1,
wherein the suction line (5) is formed at an angle in the longitudinal section, with a first horizontal portion (17) and a second vertical portion (18).

4. The dispenser as claimed in claim 1,
wherein the valve (6) is a plastic valve.

5. The dispenser as claimed in claim 1,
wherein the air compression piston (8) is movable by finger pressure for generating a desired positive pressure, in which the valve (6) opens and in which, when the valve (6) opens, a high flow rate is immediately generated in the blow-out duct (4), which brings with it a desired sucking action in the suction line (5), for emptying, via the suction line (5), the substance reservoir (3) having a freeze-dried substance (2), wherein the substance (2) is present in the form of grains with a diameter of 0.1 mm to 2 mm.

6. A method for emptying a substance reservoir having a freeze-dried substance, with the aid of a dispenser as claimed in claim 1, comprising the steps of
sucking the substance from the substance reservoir, the substance being present in the form of grains with a diameter of 0.1 to 2 mm, out by means of a suction air stream opening into the blowing stream generated by pressing with a finger and moving the air compression piston (8), and is dispensed, wherein the blowing stream is generated by moving the air compression piston (8) until a desired positive pressure arises and the valve (6) opens.

7. The method as claimed in claim 6,
wherein the support part is first lowered, then rotated in a circular direction and, when a further substance reservoir (3) is oriented with respect to a tip of the suction line (5), is raised again, with the tip (19) of the suction line (5) immediately penetrating the substance reservoir (3).

* * * * *